(12) United States Patent
Braga et al.

(10) Patent No.: US 9,713,694 B2
(45) Date of Patent: Jul. 25, 2017

(54) LOW PROFILE CATHETER ASSEMBLY

(71) Applicant: Covidien LP, Mansfield, MA (US)

(72) Inventors: Richard Braga, North Easton, MA (US); Robert Frechette, Lakeville, MA (US); Brett Haarala, Framingham, MA (US)

(73) Assignee: Covidien LP, Mansfield, MA (US)

( * ) Notice: Subject to any disclaimer, the term of this patent is extended or adjusted under 35 U.S.C. 154(b) by 162 days.

(21) Appl. No.: 13/855,051

(22) Filed: Apr. 2, 2013

(65) Prior Publication Data

US 2014/0128820 A1    May 8, 2014

Related U.S. Application Data

(63) Continuation of application No. 13/448,986, filed on Apr. 17, 2012, now Pat. No. 8,454,565, which is a
(Continued)

(51) Int. Cl.
*A61M 25/00* (2006.01)
*A61M 39/28* (2006.01)
*A61M 1/36* (2006.01)

(52) U.S. Cl.
CPC ...... *A61M 25/0097* (2013.01); *A61M 1/3653* (2013.01); *A61M 25/00* (2013.01); *A61M 25/0026* (2013.01); *A61M 39/284* (2013.01)

(58) Field of Classification Search
CPC ........ A61M 125/0097; A61M 25/0026; A61M 25/0097; A61M 1/3653
(Continued)

(56) References Cited

U.S. PATENT DOCUMENTS 1,347,931 A   7/1920 Bowes
3,698,681 A   10/1972 Lacey
(Continued)

FOREIGN PATENT DOCUMENTS

EP   1 661 597       3/1993
EP   0 554 722 A1   8/1993
(Continued)

OTHER PUBLICATIONS

European Search Report dated Jan. 18, 2008, for European Application No. EP 07 25 3789.

*Primary Examiner* — Edelmira Bosques
(74) *Attorney, Agent, or Firm* — Kenneth Collier; Jessica Kwak Rauckman

(57) ABSTRACT

A medical catheter assembly includes a catheter hub, an elongate catheter member extending from the catheter hub and having at least one longitudinal lumen for passage of fluids, an extension tube extending from the catheter hub and defining an internal lumen in fluid communication with the at least one longitudinal lumen of the catheter member and a clamp positionable about the extension tube. The catheter hub defines a reduced profile to facilitate passage of the catheter hub through a surgical tunnel. The clamp includes first and second clamp sections and defines a longitudinal clamp axis. The clamp has a longitudinal opening for passage of the extension tube and a movable member adapted to move from a first position to a second position to substantially close the internal lumen. The first and second clamp sections are separable to facilitate transverse positioning of the clamp sections about the extension tube.

25 Claims, 12 Drawing Sheets

Related U.S. Application Data continuation of application No. 11/528,913, filed on Sep. 28, 2006, now abandoned.

(58) Field of Classification Search
USPC .......................................... 604/284, 43, 534
See application file for complete search history.

(56) References Cited

U.S. PATENT DOCUMENTS

| | | | |
|---|---|---|---|
| 3,822,052 A | 7/1974 | Lange | |
| 4,193,174 A | 3/1980 | Stephens | |
| 4,403,983 A | 9/1983 | Edelman et al. | |
| 4,493,696 A | 1/1985 | Uldall | |
| 4,560,378 A | 12/1985 | Weiland | |
| 4,568,329 A | 2/1986 | Mahurkar | |
| 4,583,968 A | 4/1986 | Mahurkar | |
| 4,619,643 A | 10/1986 | Bai | |
| 4,626,240 A | 12/1986 | Edelman et al. | |
| 4,643,711 A | 2/1987 | Bates | |
| 4,692,141 A | 9/1987 | Mahurkar | |
| 4,769,005 A | 9/1988 | Ginsburg et al. | |
| 4,772,268 A | 9/1988 | Bates | |
| 4,772,269 A | 9/1988 | Twardowski et al. | |
| 4,795,439 A | 1/1989 | Guest | |
| 4,808,155 A | 2/1989 | Mahurkar | |
| 4,808,156 A | 2/1989 | Dean | |
| 4,832,687 A | 5/1989 | Smith, III | |
| 4,842,582 A | 6/1989 | Mahurkar | |
| 4,895,561 A | 1/1990 | Mahurkar | |
| 4,897,079 A | 1/1990 | Zaleski et al. | |
| 4,961,809 A | 10/1990 | Martin | |
| 4,995,865 A * | 2/1991 | Gahara et al. ................. | 604/43 |
| 5,002,552 A | 3/1991 | Casey | |
| 5,009,636 A | 4/1991 | Wortley et al. | |
| 5,035,399 A | 7/1991 | Rantanen-Lee | |
| 5,041,083 A | 8/1991 | Tsuchida et al. | |
| 5,053,004 A | 10/1991 | Markel et al. | |
| 5,053,023 A | 10/1991 | Martin | |
| 5,057,073 A | 10/1991 | Martin | |
| 5,059,170 A | 10/1991 | Cameron | |
| 5,085,632 A | 2/1992 | Ikada et al. | |
| 5,106,368 A | 4/1992 | Uldall et al. | |
| 5,135,599 A | 8/1992 | Martin et al. | |
| 5,156,592 A | 10/1992 | Martin et al. | |
| 5,167,623 A | 12/1992 | Cianci et al. | |
| 5,188,593 A | 2/1993 | Martin | |
| 5,190,520 A | 3/1993 | Fenton, Jr. et al. | |
| 5,191,881 A | 3/1993 | Beck | |
| 5,195,962 A | 3/1993 | Martin et al. | |
| 5,197,951 A | 3/1993 | Mahurkar | |
| 5,209,723 A | 5/1993 | Twardowski et al. | |
| 5,219,335 A | 6/1993 | Willard et al. | |
| 5,221,255 A | 6/1993 | Mahurkar et al. | |
| 5,221,256 A | 6/1993 | Mahurkar | |
| 5,257,978 A | 11/1993 | Haber et al. | |
| 5,308,338 A | 5/1994 | Helfrich | |
| 5,346,471 A | 9/1994 | Raulerson | |
| 5,348,536 A | 9/1994 | Young et al. | |
| 5,360,397 A | 11/1994 | Pinchuk | |
| 5,364,344 A | 11/1994 | Beattie et al. | |
| 5,374,245 A | 12/1994 | Mahurkar | |
| 5,378,230 A | 1/1995 | Mahurkar | |
| 5,380,276 A | 1/1995 | Miller et al. | |
| 5,395,316 A | 3/1995 | Martin | |
| 5,403,291 A | 4/1995 | Abrahamson | |
| 5,405,341 A | 4/1995 | Martin | |
| 5,423,769 A | 6/1995 | Jonkman et al. | |
| 5,451,206 A | 9/1995 | Young | |
| 5,464,398 A | 11/1995 | Haindl | |
| 5,472,417 A | 12/1995 | Martin et al. | |
| 5,480,380 A | 1/1996 | Martin | |
| 5,486,159 A | 1/1996 | Mahurkar | |
| 5,489,278 A | 2/1996 | Abrahamson | |
| 5,509,897 A | 4/1996 | Twardowski et al. | |
| 5,556,390 A | 9/1996 | Hicks | |
| 5,569,182 A | 10/1996 | Twardowski et al. | |
| 5,571,093 A | 11/1996 | Cruz et al. | |
| D381,420 S | 7/1997 | Musgrave et al. | |
| D384,411 S | 9/1997 | Musgrave et al. | |
| D384,741 S | 10/1997 | Musgrave et al. | |
| 5,683,640 A | 11/1997 | Miller et al. | |
| 5,685,867 A | 11/1997 | Twardowski et al. | |
| 5,702,365 A | 12/1997 | King | |
| 5,718,678 A | 2/1998 | Fleming, III | |
| 5,776,096 A | 7/1998 | Fields | |
| 5,797,869 A | 8/1998 | Martin et al. | |
| 5,807,311 A | 9/1998 | Palestrant | |
| 5,807,329 A | 9/1998 | Gelman | |
| 5,810,789 A | 9/1998 | Powers et al. | |
| 5,830,184 A | 11/1998 | Basta | |
| 5,830,196 A | 11/1998 | Hicks | |
| 5,868,717 A | 2/1999 | Prosl | |
| 5,944,732 A | 8/1999 | Raulerson | |
| 5,947,953 A | 9/1999 | Ash et al. | |
| 5,961,485 A | 10/1999 | Martin | |
| 5,961,486 A | 10/1999 | Twardowski et al. | |
| 5,976,103 A | 11/1999 | Martin | |
| 5,989,206 A | 11/1999 | Prosl et al. | |
| 5,989,213 A | 11/1999 | Maginot | |
| 5,993,437 A | 11/1999 | Raoz | |
| 6,001,079 A | 12/1999 | Pourchez | |
| 6,004,310 A | 12/1999 | Bardsley et al. | |
| 6,099,519 A | 8/2000 | Olsen et al. | |
| 6,113,062 A | 9/2000 | Schnell et al. | |
| 6,123,725 A | 9/2000 | Aboul-Hosn | |
| 6,126,631 A | 10/2000 | Loggie | |
| 6,146,354 A | 11/2000 | Beil | |
| 6,156,016 A | 12/2000 | Maginot | |
| 6,190,349 B1 | 2/2001 | Ash et al. | |
| 6,190,371 B1 | 2/2001 | Maginot et al. | |
| 6,206,849 B1 | 3/2001 | Martin et al. | |
| 6,273,875 B1 | 8/2001 | Siman et al. | |
| 6,280,423 B1 | 8/2001 | Davey et al. | |
| 6,293,927 B1 | 9/2001 | McGuckin, Jr. | |
| 6,342,120 B1 | 1/2002 | Basta | |
| 6,346,090 B1 | 2/2002 | Liska et al. | |
| 6,394,141 B2 | 5/2002 | Wages et al. | |
| 6,409,700 B1 | 6/2002 | Siegel, Jr. et al. | |
| 6,447,488 B2 | 9/2002 | Estabrook et al. | |
| 6,461,321 B1 | 10/2002 | Quinn | |
| 6,475,207 B1 | 11/2002 | Maginot et al. | |
| 6,482,169 B1 | 11/2002 | Kuhle | |
| 6,506,182 B2 | 1/2003 | Estabrook et al. | |
| 6,579,261 B1 | 6/2003 | Kawamura | |
| 6,585,705 B1 | 7/2003 | Maginot et al. | |
| 6,592,542 B2 | 7/2003 | Childers et al. | |
| 6,592,558 B2 | 7/2003 | Quah | |
| 6,595,966 B2 | 7/2003 | Davey et al. | |
| 6,620,118 B1 | 9/2003 | Prosl et al. | |
| 6,638,242 B2 | 10/2003 | Wilson et al. | |
| 6,692,473 B2 | 2/2004 | St. Cyr et al. | |
| 6,695,832 B2 | 2/2004 | Schon et al. | |
| 6,719,749 B1 | 4/2004 | Schweikert et al. | |
| 6,723,084 B1 | 4/2004 | Maginot et al. | |
| 6,730,096 B2 | 5/2004 | Basta | |
| 6,743,218 B2 | 6/2004 | Maginot et al. | |
| 6,749,580 B2 | 6/2004 | Work et al. | |
| 6,758,836 B2 | 7/2004 | Zawacki | |
| 6,786,884 B1 | 9/2004 | DeCant, Jr. et al. | |
| 6,808,510 B1 | 10/2004 | DiFiore | |
| 6,814,718 B2 | 11/2004 | McGuckin, Jr. et al. | |
| 6,858,019 B2 | 2/2005 | McGuckin, Jr. et al. | |
| 6,872,198 B1 | 3/2005 | Wilson et al. | |
| 6,911,014 B2 | 6/2005 | Wentling et al. | |
| 6,921,396 B1 | 7/2005 | Wilson et al. | |
| 6,942,635 B2 | 9/2005 | Rosenblatt et al. | |
| 6,942,653 B2 | 9/2005 | Quinn | |
| 6,966,886 B2 | 11/2005 | Appling | |
| 6,969,381 B2 | 11/2005 | Voorhees | |
| 6,976,973 B1 | 12/2005 | Ruddell et al. | |
| 6,986,752 B2 | 1/2006 | McGuckin, Jr. et al. | |
| 6,991,625 B1 | 1/2006 | Gately et al. | |
| 7,008,395 B1 | 3/2006 | Loggie | |
| 7,008,412 B2 | 3/2006 | Maginot | |

(56) References Cited

U.S. PATENT DOCUMENTS

| | | |
|---|---|---|
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,749,185 B2 | 7/2010 | Wilson et al. |
| 2001/0049507 A1 | 12/2001 | Ishida et al. |
| 2002/0099326 A1 | 7/2002 | Wilson et al. |
| 2003/0093029 A1 | 5/2003 | McGuckin, Jr. et al. |
| 2004/0092887 A1 | 5/2004 | Nickels |
| 2004/0249337 A1 | 12/2004 | DiFiore |
| 2005/0033222 A1 | 2/2005 | Haggstrom et al. |
| 2005/0080398 A1 | 4/2005 | Markel et al. |
| 2005/0085765 A1 | 4/2005 | Voorhees |
| 2005/0090776 A1 | 4/2005 | McGuckin et al. |
| 2005/0215978 A1 | 9/2005 | Ash |
| 2005/0228339 A1 | 10/2005 | Clark |
| 2005/0253390 A1 | 11/2005 | Blazek |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2006/0276773 A1* | 12/2006 | Wilson ............... A61M 25/0097 604/523 |

FOREIGN PATENT DOCUMENTS

| | | |
|---|---|---|
| EP | 0 322 225 B1 | 2/1995 |
| EP | 0 713 406 B1 | 3/1998 |
| EP | 0 570 530 B1 | 8/1999 |
| EP | 0 555 780 B1 | 9/1999 |
| EP | 1 144 039 B1 | 12/2005 |
| WO | WO 95/04567 A1 | 2/1995 |
| WO | WO 97/22374 | 6/1997 |
| WO | WO 97/37699 A1 | 10/1997 |
| WO | WO 98/41277 | 9/1998 |
| WO | WO 99/38550 | 8/1999 |
| WO | WO 99/65557 | 12/1999 |
| WO | WO 00/77428 | 12/2000 |
| WO | WO 01/37901 | 5/2001 |
| WO | WO 01/91845 A1 | 12/2001 |
| WO | WO 02/13899 A1 | 2/2002 |
| WO | WO 02/18004 A3 | 3/2002 |
| WO | WO 03/033049 A3 | 4/2003 |
| WO | WO 03/066148 A1 | 8/2003 |
| WO | WO 2004/093958 A1 | 11/2004 |
| WO | WO 2005/023336 A2 | 3/2005 |
| WO | WO 2005/077449 A1 | 8/2005 |
| WO | WO 2005/084741 A1 | 9/2005 |
| WO | WO 2006/014339 A2 | 2/2006 |
| WO | WO 2006/081489 | 8/2006 |

* cited by examiner

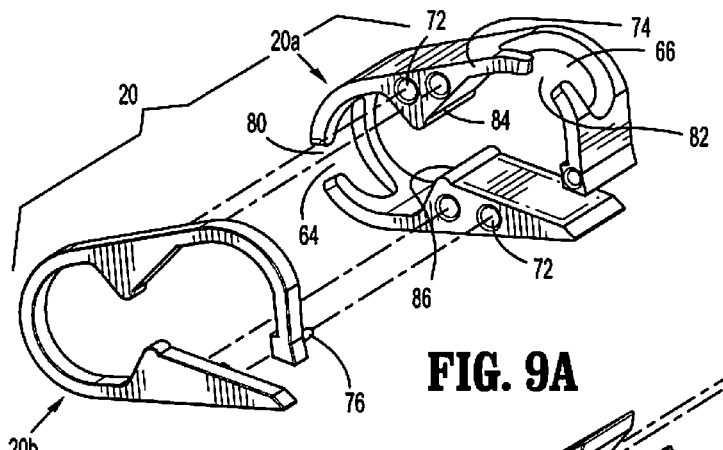
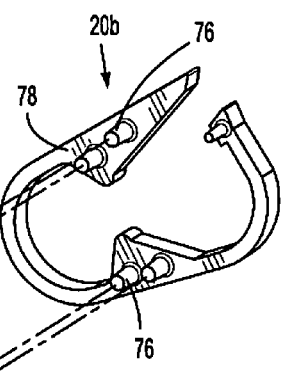
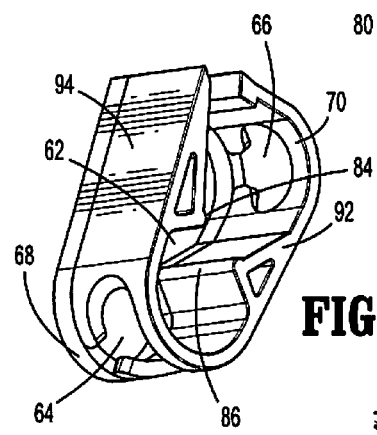
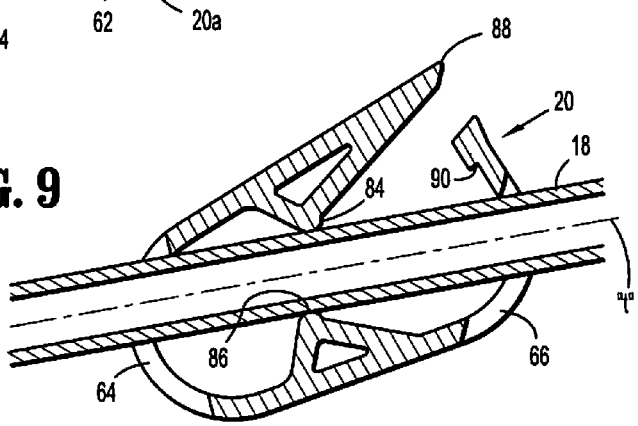
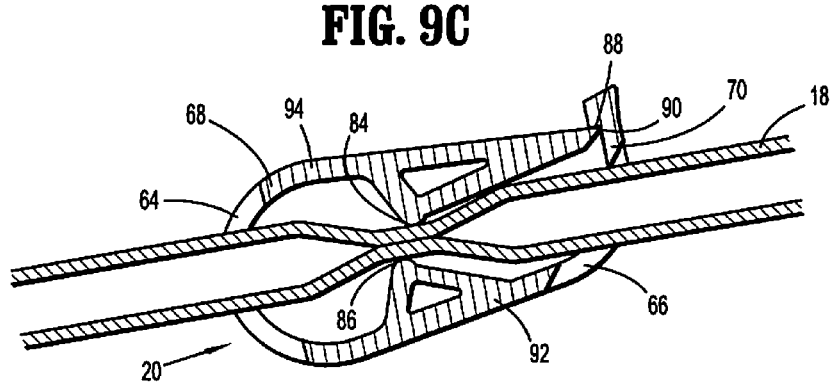
FIG. 9A
FIG. 9B
FIG. 9
FIG. 9C
FIG. 9D

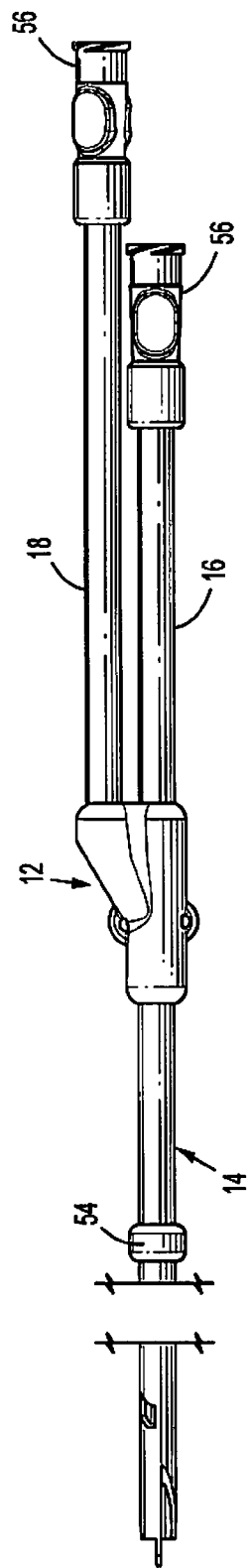
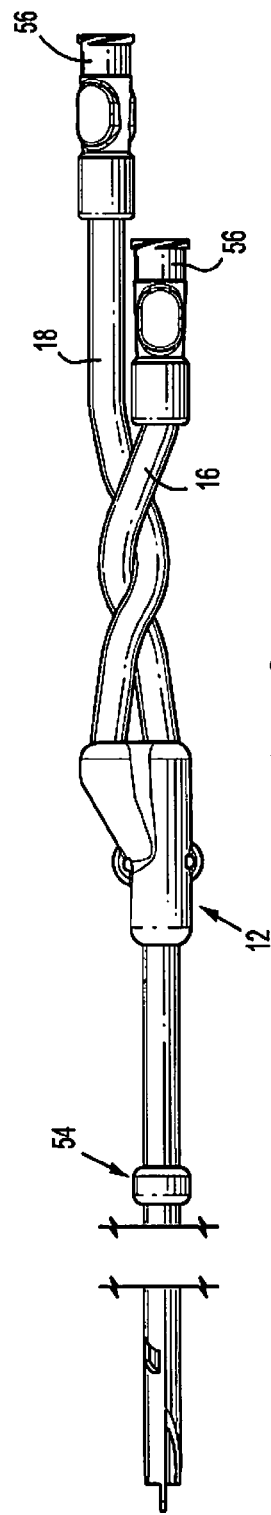
FIG. 11
FIG. 12

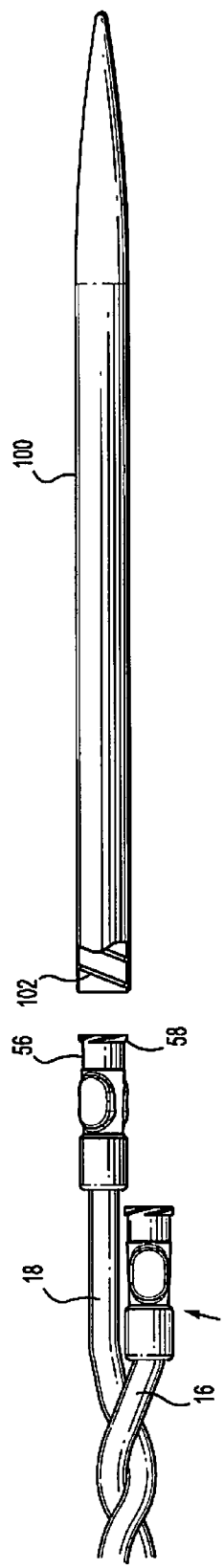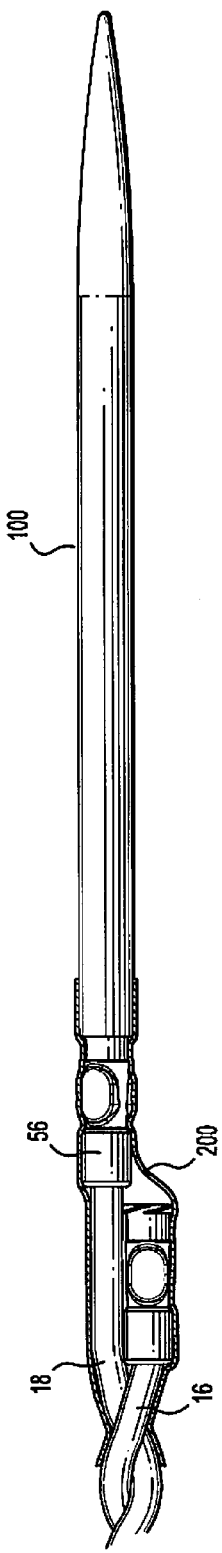
FIG. 13
FIG. 14

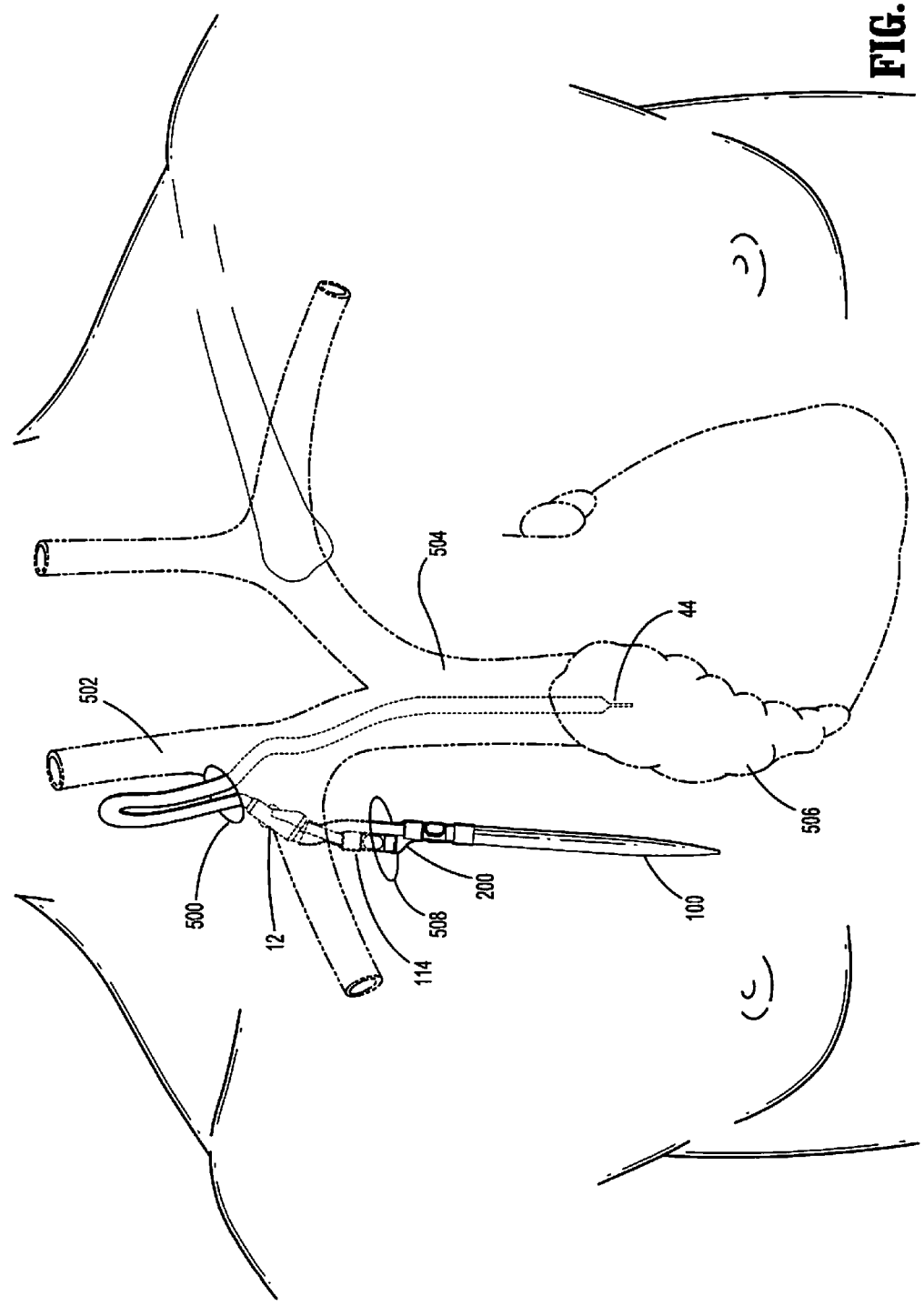

LOW PROFILE CATHETER ASSEMBLY

CROSS-REFERENCE TO RELATED APPLICATION

This application is a continuation application of U.S. application Ser. No. 13/448,986, filed Apr. 17, 2012, which is a continuation of U.S. application Ser. No. 11/528,913, filed Sep. 28, 2006, now abandoned, the entire contents of each of which are hereby incorporated herein by reference.

BACKGROUND

1. Technical Field

The present disclosure is directed to a catheter assembly, and, in particular, relates to a low-profile catheter system adapted for use in a subcutaneous tunneling catheterization procedure.

2. Description of the Related Art

Catheters are flexible medical instruments intended for the withdrawal and introduction of fluids relative to body cavities, ducts, and vessels. Catheter instrumentation may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste, and toxins. The dialyzed blood is returned to the patient through a venous lumen of the catheter.

Various techniques are employed for the insertion of hemodialysis catheters including, e.g., with the use of guidewires, introduction stylets or the like. Some of these known techniques include subcutaneous tunneling methodologies where a subcutaneous tunnel is formed between two spaced openings in the skin with the use of a trocar or the like. The catheter end is attached to the trocar and pulled though the tunnel to expose the catheter which is subsequently inserted into, e.g., the jugular vein and routed to the heart.

SUMMARY

Accordingly, the present disclosure is directed to further improvements in hemodialysis catheters and systems used therewith. A medical catheter assembly includes a catheter hub having a reduced profile, an elongate catheter member extending from the catheter hub and having at least one longitudinal lumen for passage of fluids, an extension tube extending from the catheter hub and defining an internal lumen in fluid communication with the at least one longitudinal lumen of the catheter member and a clamp positionable about the extension tube. The clamp includes first and second clamp sections and defines a longitudinal clamp axis. The clamp has a longitudinal opening for passage of the extension tube and a movable member adapted to move from a first position to a second position to substantially close the internal lumen. The first and second clamp sections are separable to facilitate positioning of the extension tube within the longitudinal opening, e.g., subsequent to positioning the elongate catheter member within the subject. The first and second clamp sections may be releasably mounted to each other along the longitudinal clamp axis to facilitate lateral positioning of the extension tube within the longitudinal opening of the clamp. The first and second clamp sections may include a pin and corresponding slot mechanism for effecting releasable mounting of the first and second clamp sections. The first and second clamp sections may be connected by a tether.

In one preferred embodiment, the clamp includes a clamp base defining the longitudinal opening and has the movable member mounted thereto. The movable member is pivotally mounted to the clamp base and is adapted to pivot relative to clamp base between the first and second positions thereof. Means for releasably securing the movable member in the second position may be provided. The clamp base may include an internal locking shelf dimensioned to engage the movable member to secure the movable member in the second position.

The medical catheter assembly may include first and second extension tubes which are connectable to the catheter hub. The catheter hub defines first and second extension conduits for respectively receiving the first and second extension tubes. The first and second extension conduits may be arranged in side by side relation. Preferably, the first extension conduit is arranged about an axis in substantial parallel relation with a longitudinal hub axis of the catheter hub. The second extension conduit is arranged about an axis in oblique relation with the longitudinal hub axis of the catheter hub. First and second adapters may be mounted to each of the first and second extension tubes. The first extension tube and the first adapter define a first effective length which is substantially less than a corresponding second effective length of the second extension tube and the second adapter. Preferably, the first effective length is less than a length of the second extension tube to permit the first extension tube and the first adapter to be positioned in adjacent side by side relation with respect to the second extension tube thereby reducing the profile thereof to facilitate passage through tissue.

The catheter hub may define a pair of suture wing holes for receiving a suture utilized in securing the catheter hub. Alternatively, the catheter hub defines an outer groove dimensioned for accommodating a suture utilized in securing the catheter hub.

In another embodiment, a low profile catheter hub for an elongate dual lumen catheter includes a catheter hub member adapted for connection to a dual lumen catheter. The catheter hub member defines a longitudinal hub axis and has first and second conduits therein adapted for fluid connection to respective fluid supply and/or withdrawal tubing. The first fluid conduit is arranged about a first axis extending in substantial parallel relation with the longitudinal hub axis. The second fluid conduit is arranged about a second axis in oblique relation with the longitudinal axis.

A clamp for closing compressible medical tubing is also provided. The clamp includes a clamp member defining a longitudinal clamp axis. The clamp member includes first and second clamp sections and has a longitudinal opening for passage of compressible tubing. The clamp member includes a movable member adapted to move from a first position to a second position to substantially close a lumen of the compressible tubing. The first and second clamp sections are releasably mountable to each other whereby the first and second clamp sections may be separable generally along the longitudinal clamp axis to permit access to the longitudinal opening to facilitate positioning of the compressible tubing within the longitudinal opening. The first and second clamp sections may be connected by a tether.

The first and second clamp sections include a pin and corresponding slot mechanism for providing a releasable mounting of the first and second clamp sections. The clamp member may include a clamp base defining the longitudinal opening and having the movable member pivotally mounted thereto. The movable member is adapted to pivot relative to the clamp base between the first and second positions thereof. The clamp base may include an internal locking shelf dimensioned to engage the movable member to secure the movable member in the second position.

A method for performing a surgical procedure is also disclosed. The method includes the steps of:

providing a catheter including a catheter hub and an elongated catheter extending from the hub, the elongated catheter having at least one longitudinal lumen for passage of fluids;

accessing an underlying tissue site through an opening in the skin of a patient;

advancing a distal end of the elongated catheter through the tissue site and into the patient;

creating a surgical tunnel from the tissue site and out through a second opening in the skin remote from the first opening;

passing the catheter through the surgical tunnel by introducing the catheter hub through the first opening and advancing the catheter hub with the elongated catheter following there along within the surgical tunnel; and fluidly coupling the at least one longitudinal lumen of the catheter with an external fluid source.

BRIEF DESCRIPTION OF THE DRAWINGS

Preferred embodiments of the disclosure will be better understood with reference to the accompanying drawings wherein:

FIG. 9 is a perspective view of the clamp of the low-profile catheter;

FIGS. 9A-9B are each perspective views illustrating the clamp of FIG. 9 in a non-assembled condition;

FIG. 9C is a view of an area of detail identified in FIG. 3 illustrating the clamp positioned about the extension tube and in a first open position;

FIG. 9D is a view similar to the view of FIG. 9C illustrating the clamp in a second closed position;

FIG. 11 is a side plan view of the low profile catheter with the clamps removed;

FIG. 12 is a side plan view similar to the view of FIG. 11 with the extension tubes twisted prior to insertion within the surgical site;

FIG. 13 is a side plan view illustrating a tunneling instrument and the extension tube adapter;

FIG. 14 is a side plan view illustrating the tunneling instrument mounted to the extension tube adapter and a sheath positioned about the connection location.

FIGS. 16-17 are views illustrating a methodology of insertion of the low profile catheter through a reverse tunneling procedure to access the right atrium of the heart.

DETAILED DESCRIPTION OF THE PREFERRED EMBODIMENTS

The exemplary embodiments of the catheter and methods of use disclosed are discussed in terms of medical catheters for the administration of fluids (withdrawal or introduction) relative to the body of a subject and, more particularly, in terms of a hemodialysis catheter. However, it is envisioned that the present disclosure may be employed with a range of catheter applications including surgical, diagnostic and related treatments of diseases and body ailments of a subject. It is further envisioned that the principles relating to the catheter disclosed include employment with various catheter related procedures, such as, for example, hemodialysis, cardiac, abdominal, urinary, intestinal, and in chronic and acute applications. Moreover, the catheter can be used for administration of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

The following discussion includes a description of the catheter system, followed by a description of an exemplary method of operating the catheter in accordance with the principles of the present disclosure. For discussion purposes, the catheter will be discussed in terms of a hemodialysis catheter and the method of operation will be discussed in terms of a reverse tunneling procedure utilized for positioning the catheter during a dialysis procedure. However, those skilled in the art will appreciate the catheter has many other applications in addition to dialysis applications.

Figure 1:
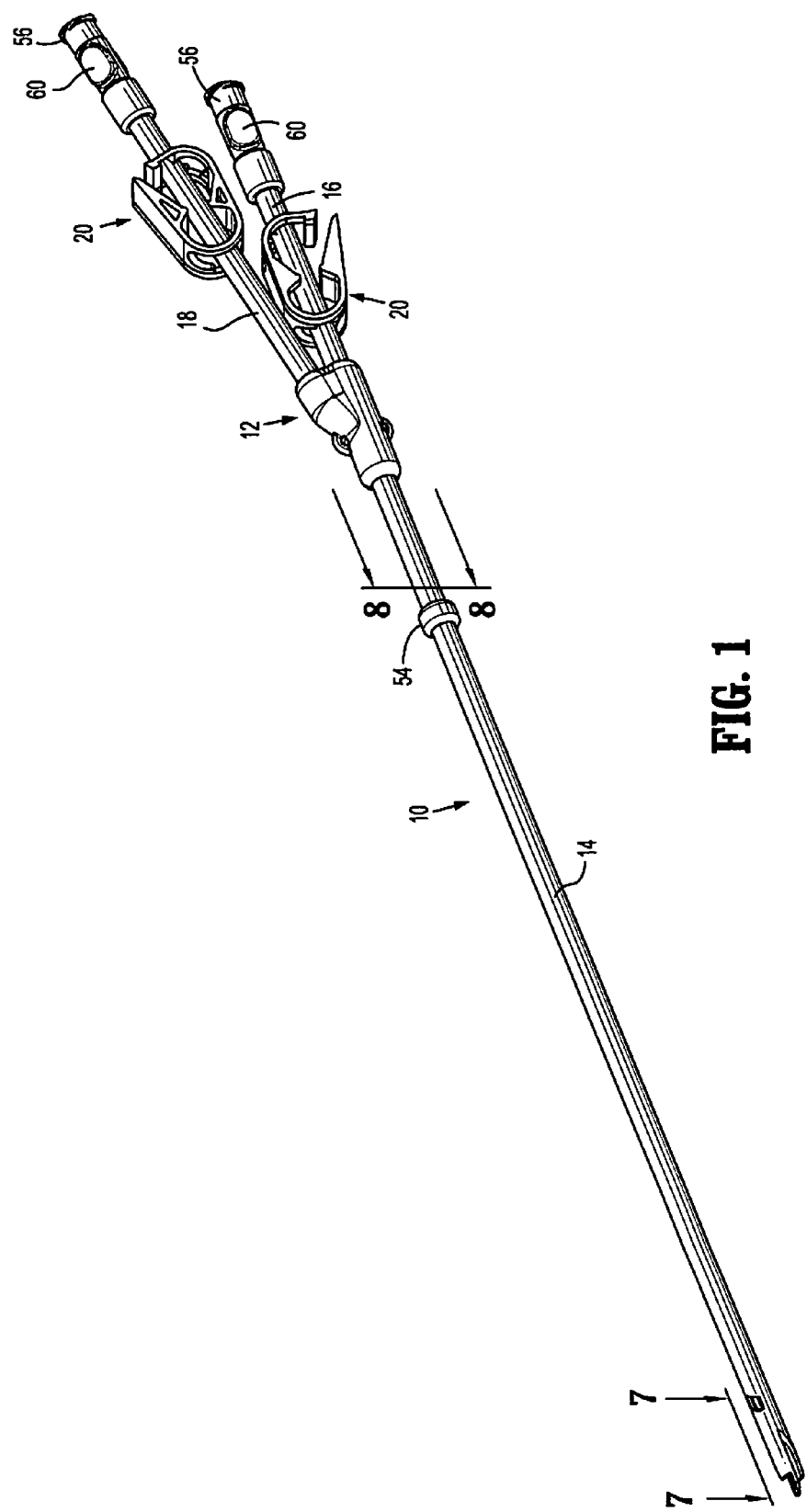
FIG. 1 is a perspective view of the low-profile catheter of the system in accordance with the principles of the present disclosure.
Figure 2:
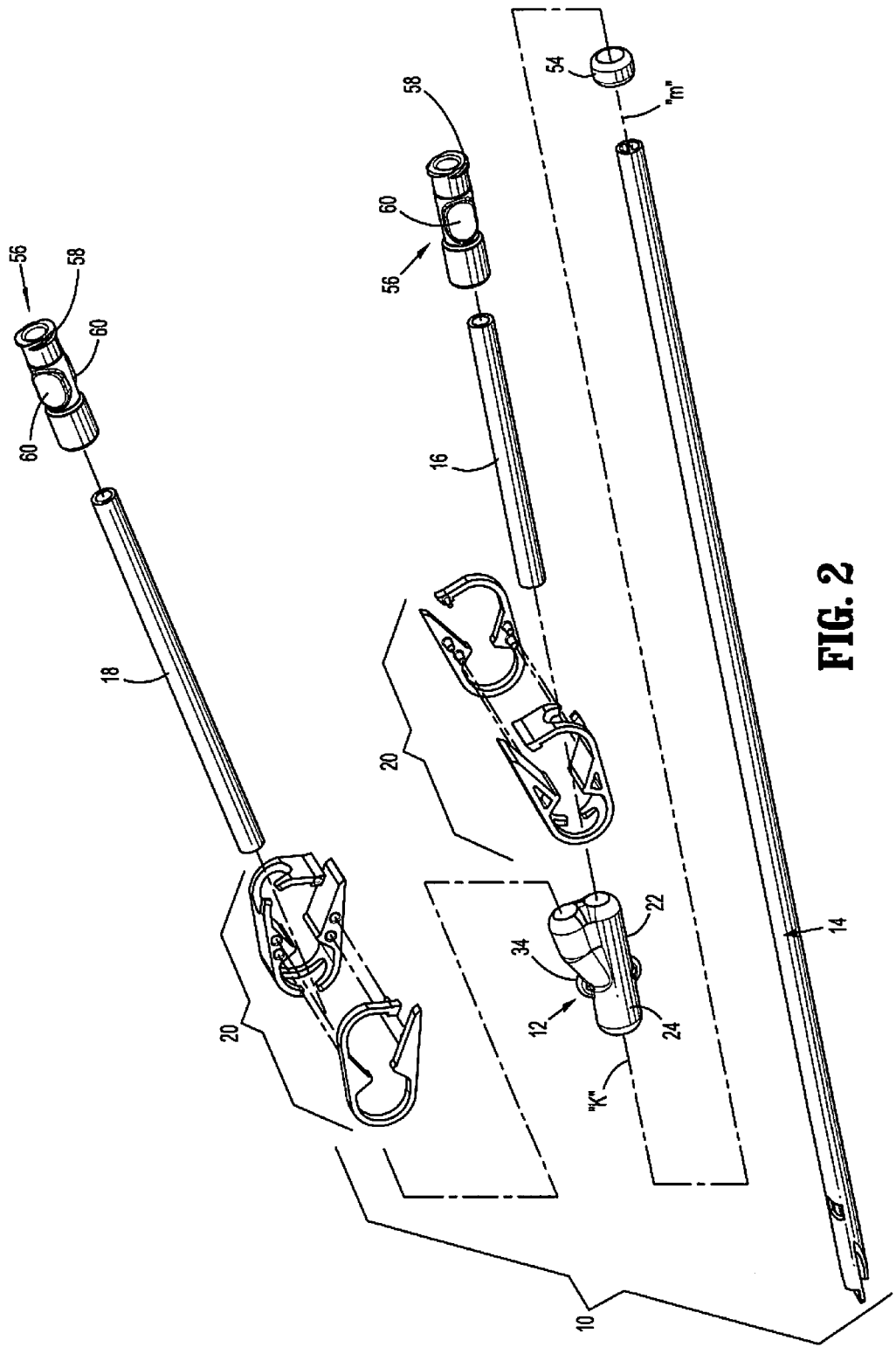
FIG. 2 is a perspective view with parts separated illustrating the components of the low-profile catheter of FIG. 1.

Referring now to the figures wherein like components are designated by like reference numerals throughout the several views, FIGS. 1-2 illustrate in perspective views, the hemodialysis catheter 10 in accordance with the principles of the system of the present disclosure. Catheter 10 includes several components assembled together, namely, catheter hub or housing 12, elongated catheter member 14 extending distally from the catheter hub 12 and first and second extension tubes 16, 18 extending proximally from the catheter hub 12. Catheter system 10 further includes a pair of clamps 20 which are mountable about each of extension tubes 16, 18.

Figure 3:
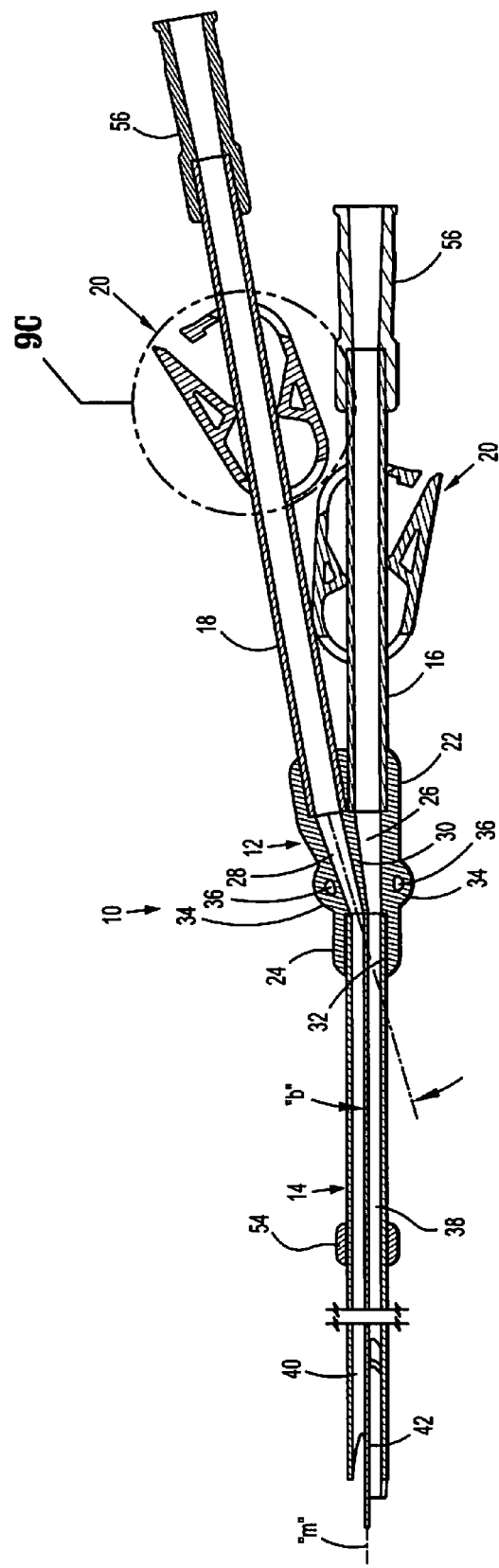
FIG. 3 is a side cross-sectional view of the low-profile catheter.

With reference now to FIGS. 1-3, catheter hub 12 is advantageously dimensioned for engagement by the clinician. Moreover, catheter hub 12 defines a reduced profile particularly when viewed along the longitudinal housing axis "k" (FIG. 2) of the catheter hub 12. Housing axis "k" is in general alignment with axis "m" of catheter member 14. Catheter hub 12 includes proximal or trailing housing section 22 adjacent extension tubes 16, 18 and distal or leading housing section 24 adjacent catheter member 14. As best depicted in FIG. 3, proximal housing section 22 defines first and second internal extension conduits 26, 28 extending along the housing axis "k" and separated by septum wall 30 of catheter hub 12. First extension conduit 26 is in general parallel relation with the housing axis "k". Second extension conduit 28 is arranged at an acute angle "b" with respect to the housing axis "k". Angle "b" may range from about 0 degrees to about 45 degrees relative to the housing axis "k", more preferably, about 5 degrees to about 20 degrees relative to the housing axis "k". This parallel arrangement of first extension conduit 26 coupled with the slight oblique arrangement of second extension conduit 28 significantly reduces the profile of catheter hub 12 particularly compared to conventional catheter hub designs which employ a v-or t-shaped shaped conduit connection areas.

First and second extension conduits 26, 28 are adapted to receive respective first and second extension tubes 16, 18 in secured relation therewith. In one preferred embodiment, extension tubes 16, 18 are secured within the respective extension conduits 26, 28 via an interference or frictional fit. It is also envisioned that cements or adhesives may be utilized to secure extension tubes 16, 18 within their respective extension conduits 26, 28. Distal or leading housing section 24 of catheter hub 12 defines central opening 32 which receives catheter member 14. Catheter member 14 may be secured within central opening 32 of distal housing section 24 via an interference or frictional fit, and, possibly supplemented with cements and adhesives or the like.

Figure 4:
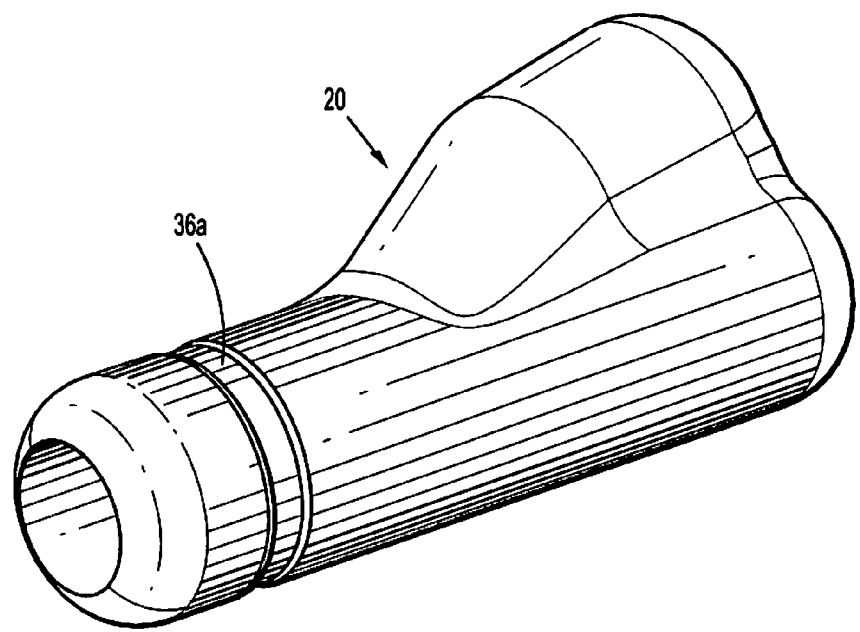
FIG. 4 is a perspective view of an alternate embodiment of the catheter hub of the low profile catheter.

Catheter hub 12 may further include a pair of opposed suture wings 34 along its outer surface. Suture wings 34 define openings 36 dimensioned for receiving sutures which may be utilized in securing catheter hub 20 relative to the subject. In an alternative embodiment depicted in FIG. 4, catheter hub 20 may have an annular groove 36a in its outer wall in lieu of suture wings 34. A suture may be wrapped within annular groove 36a and subsequently secured relative to the subject.

Referring now to FIGS. 5-8, in conjunction with FIG. 3, elongated catheter member 14 will be discussed. Catheter member 14 is preferably a dual lumen catheter having first and second longitudinal lumens 38,40 separated by a septum wall 42 which extends the length the catheter member 14 (FIG. 3). Each of the first and second longitudinal lumens 38, 40 may define a D-shaped opening in cross-section. Other lumen arrangements are also envisioned including circular, pie shaped or other shapes known in the art. Coaxial lumens are also envisioned. Septum wall 42 of catheter member 14 preferably abuts septum wall 30 of catheter hub 20 in the assembled condition of the components. Thus, with this arrangement, low profile catheter 10 defines a dual lumen catheter, inclusive of a first lumen including extension conduit 26 and first longitudinal lumen 38 of catheter member 14, and a second lumen inclusive of extension conduit 28 and second longitudinal lumen 40. Single or triple lumen catheters are also envisioned.

Figure 5:
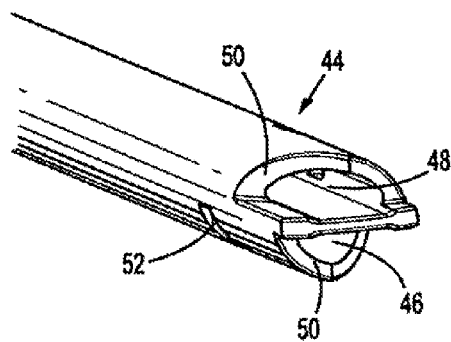
FIGS. 5-6 are perspective views illustrating the leading end of the low profile catheter.
Figure 6:
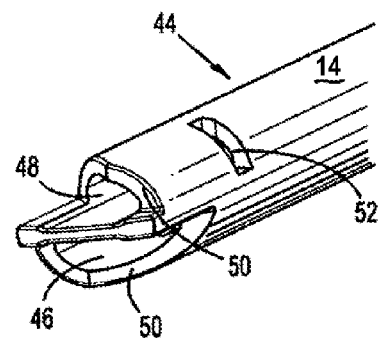
Figure 7:
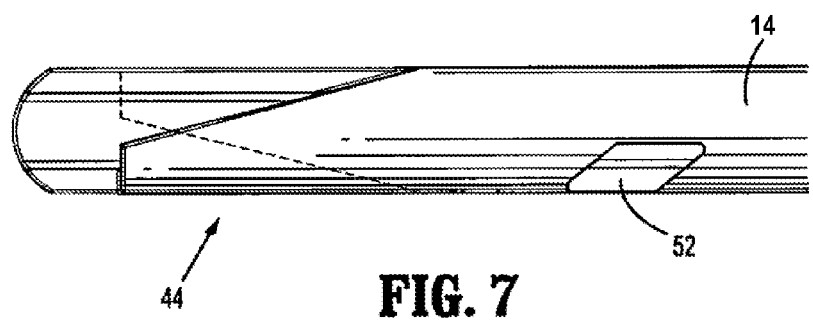
FIG. 7 is a side plan view of the leading end of the low profile catheter system taken along the lines 7-7 of FIG. 1.
Figure 8:
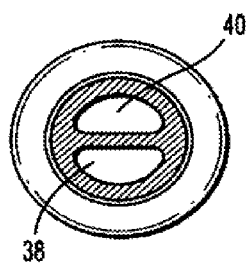
FIG. 8 is a cross-sectional view of the low profile catheter taken along the lines 8-8 of FIG. 1.

With particular reference to FIGS. 5-7, leading or distal end 44 of catheter member 14 will be discussed. The arrangement of catheter distal end 44 is similar to an embodiment disclosed in commonly assigned U.S. Patent Application No. 2005/0267400 to Haarala et al., the entire contents of which are incorporated herein by reference. In particular, distal end 44 of catheter member 14 includes a pair of opposed openings 46, 48 arranged in its outer wall in diametrical relation and in fluid communication with respective first and second longitudinal lumens 38, 40. Each opening 46, 48 is characterized by having an arcuate recessed wall surface 50 to define a partial generally arcuate opening as shown. Openings 46, 48 are symmetrically arranged about the longitudinal axis "m" of catheter member 14. Preferably, septum wall 42 of catheter member 14 extends distally beyond catheter member 14. Catheter member 14 further includes a pair of polygonal or parallelepiped openings 52 in fluid communication with first and second longitudinal lumens 38, 40 and openings 46, 48. Openings 52 are disposed proximal of openings 46, 48 as shown. Openings 46, 48 and proximal openings 52 permit passage of fluids during the surgical procedure. Further details regarding distal end 44 of catheter member 14 may be ascertained by reference to the Haarala '400 publication. Other arrangements, e.g., as disclosed as alternate embodiments in the Haarala '400 publication, are also envisioned.

Catheter member 14 is preferably flexible and may be formed by conventional injection molding or extrusion means. The wall of catheter member 14 may include reinforcing material if desired. Catheter member 14 may have a pre-curved configuration in its normal state, i.e., have a preformed bend which it normally assumes in the absence of an external stressor to conform to a body cavity or vessel in which the catheter member is to be positioned. Alternatively, catheter member 14 may be devoid of any normally curved orientation.

Referring again to FIGS. 1-3, catheter member 14 may further include at least one cuff 54 on its outer surface. Cuff 54 may include a fabric material and functions to be a site for tissue ingrowth for long term securing of catheter 10 in an indwelling position. For example, cuff 54 may reside in the tunnel formed during the tunneling procedure. More than one cuff 54 may also be provided. Catheter member 14 may also include radiopaque markings or strips to facilitate the location of catheter within the body with a fluoroscope.

First and second extension tubes 16,18 may be any suitable tubing adapted to supply or withdrawal fluid to or from a body vessel. First and second extension tubes 16,18 preferably include a compressible material whereby the tubes 16,18 may be selectively compressed via clamps 20 to substantially close the opening within the tubes 16,18. The free or trailing ends of extension tubes 16,18 remote from catheter hub 12 have adapters 56 mounted thereto. Adapters 56 may be any conventional luer connector or adapter utilized in a surgical environment for administrating fluids. One suitable connection is a luer connector which may incorporate an external thread or cam 58 for securing to a fluid source. Adapters 56 may be secured to extension tubes 16,18 by any of the aforementioned means including friction or tolerance fit, adhesives, cements, or the like.

As best depicted in FIGS. 1-2, adapters 56 each include outer walls having a pair of recessed surfaces 60. Recessed surfaces 60 are ergonomically designed to be engaged by the clinician thereby facilitating manipulation of the catheter 10 about the operative site.

First tube extension 16 may define a length which is less than second tube extension 18. In one preferred embodiment, the overall effective length of first extension tube 16 and its attached adapter 56 is less than the corresponding overall effective length of second extension tube 18 and its adapter 56. As a further preference, the overall effective length of first extension tube 16 and its adapter 56 is less than or equal to the length of second extension tube 18. With this arrangement, first extension tube 16 and its adapter 56 may be placed in juxtaposed or side-by-side relation with the second extension tube 18 to substantially reduce the profile presented by the first and second extension tubes 16, 18. The significance of this feature will be appreciated from the description provided hereinbelow. First and second extension tubes 16,18 may define the same lengths if desired.

Referring now to FIGS. 9-9D, in conjunction with FIG. 3, clamps 20 will be discussed. Clamps 20 are mounted about first and second extension tubes 16,18. Each clamp 20 is adapted to move from a first open position in non compressive engagement with the respective extension tube 16,18 (FIG. 9C) to a second substantially closed position to compress the respective extension tube (16, 18) and close the lumen within the tube (FIG. 9D) thereby preventing fluid flow in either direction. Each clamp 20 defines a longitudinal clamp axis "t" and longitudinal opening or passage 62 for reception of extension tube 16,18. Longitudinal passage 62 is inclusive of first and second openings 64, 66 within opposed end walls 68,70 of the clamp 20 and the central interior of the clamp 20.

Each clamp 20 includes two sections, namely, first clamp section 20a and second clamp section 20b which is releasably mountable to the first clamp section. In one preferred arrangement, first clamp section 20a includes openings 72 in side wall 74. Second clamp section 20b includes pins 76 extending in transverse relation from side wall 78. Pins 76 are advantageously dimensioned to be received in the openings 72 of first clamp section 20a in snap relation therewith whereby, upon mounting of the second clamp section 20b to the first clamp section 20a, the clamp 20 becomes a single unit. Preferably, in use, the respective extension tube 16,18 is positioned through the cutaway portions 80,82 (FIG. 9A) leading to respective openings 14,16 of the first clamp section 20a. Thereafter, second clamp section 20b is mounted to first clamp section 20a as discussed hereinabove.

Clamp 20 further includes internal wedge surfaces 84,86 arranged in opposed relation as shown. Upon movement of clamp 20 from the first open position of FIG. 9C to the second closed position of FIG. 9D, wedge surfaces 84,86 engage extension tube 16, 18 in a manner to close the opening within the extension tube 16, 18 to thereby prevent passage of fluid within the tube 16,18. Clamp 20 further includes a locking mechanism to secure clamp 20 in the in the second closed position. The locking mechanism preferably includes locking surface 88 disposed on the cantilevered section of clamp 20 which engages locking ledge 90 to secure the clamp 20 in the second closed position. In general, clamp 20 includes clamp base 92 having wedge surface 86 and movable member 94 having wedge surface 84 mounted via a pivoting, hinge, living hinge, or cantilever arrangement to the clamp base 92. Movable member 94 is adapted to move or pivot between the first open position and the second closed position of FIGS. 9C, 9D respectively.

Figure 10B:
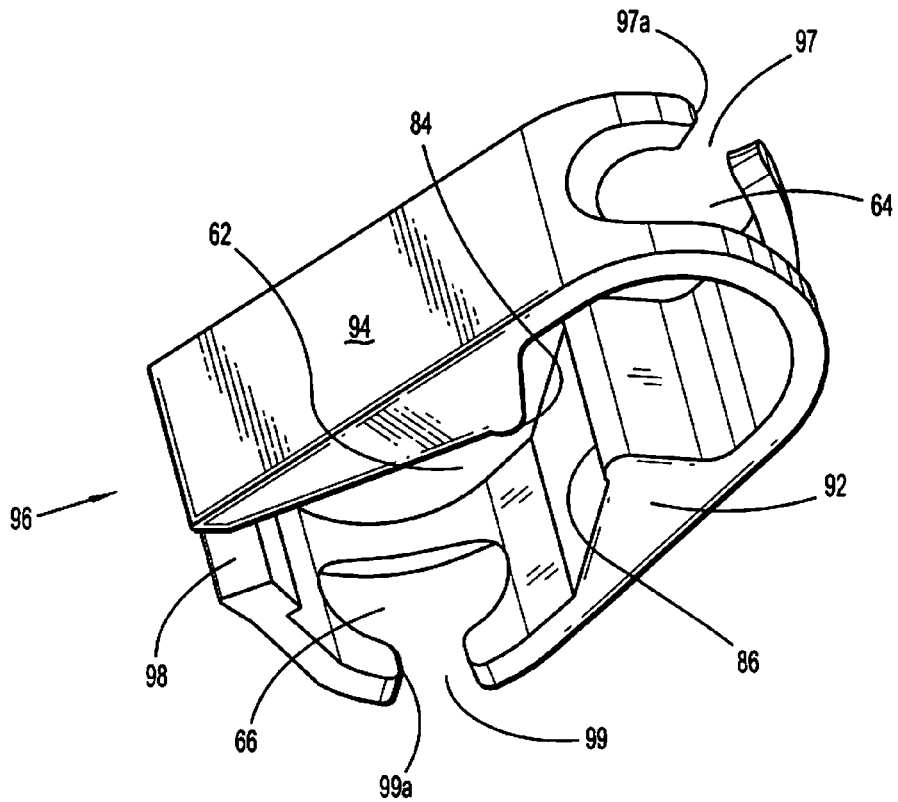
FIGS. 10A and 10B are perspective views of alternate embodiments of the clamp.
Figure 10A:
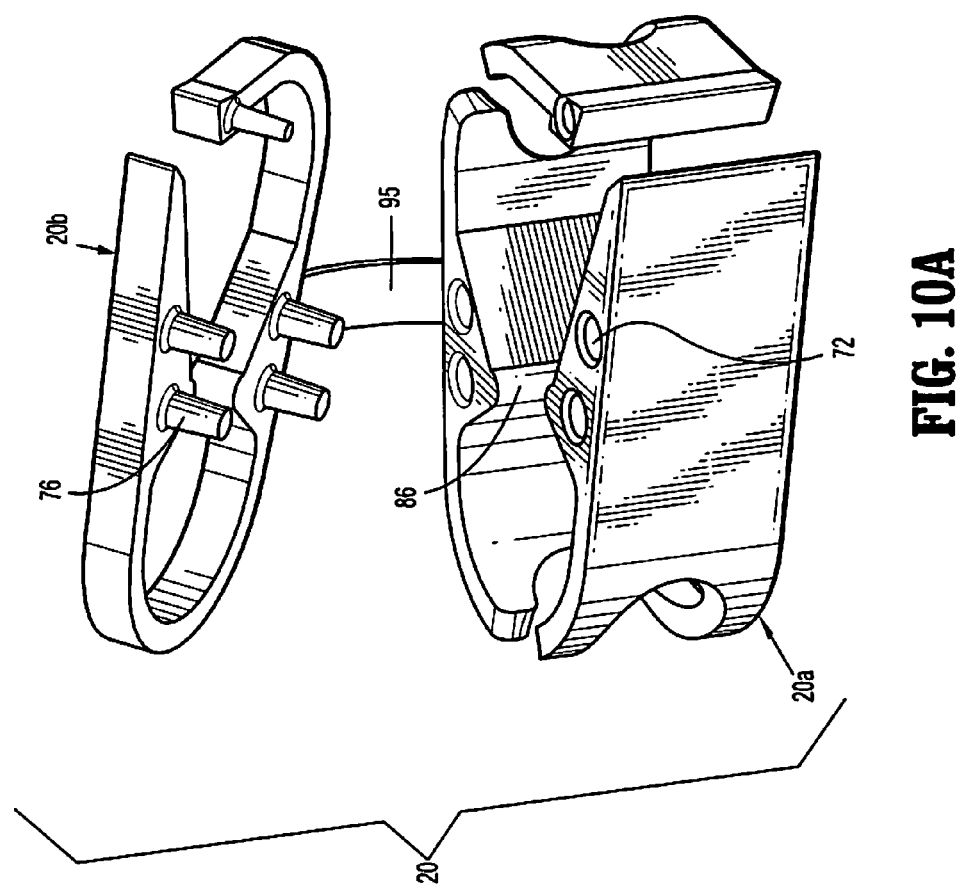

FIG. 10A illustrates an alternate embodiment of the clamp. Clamp 20 is substantially similar to the clamp 20 described in connection with FIGS. 9-9D. However, in accordance with this embodiment, clamp 20 further includes tether 95 connected to clamp sections 20a, 20b. Tether 95 may be integrally connected to clamp sections 20a, 20b or monolithically formed with the clamp sections 20a, 20b. Tether 95 functions to operatively couple clamp components 20a, 20b to facilitate manipulation and/or connection of the clamp components at the operative site.

FIG. 10B illustrates an alternate embodiment of clamp 20. Clamp 96 is substantially similar to clamp 20 discussed hereinabove, but is a single piece component. Clamp 96 further defines cut away portions 97,99 on opposed lateral sides of clamp 96 in communication with openings 64,66 respectively. It is also envisioned that cut away portions 97,99 may be on the same side of clamp 96. Thus, clamp 96 may be mounted about an extension tube 16,18 by passing the tube between movable member 94 and base member 92 through spacing 98 with clamp 96 in the open position of FIG. 10B. Sections of the respective tubing 16,18 may be passed through cut away portions 97,99 for reception within openings 64, 66. In one embodiment, portions 97a,99a of clamp base 92 defining respective cut away portions 97,99 are relatively narrow adjacent one lateral side to facilitate retention of the tube upon positioning of the tube within longitudinal passage 62 of clamp 20. Clamp 96 functions substantially in a similar manner to that described in connection with clamp 20.

The components of catheter 10 are fabricated from materials suitable for medical applications, such as, for example, polymerics or metals. Suitable metals include titanium or stainless steel, depending on the particular catheter application and/or preference of a practitioner. Semi-rigid and rigid polymerics are contemplated for fabrication, as well as resilient materials, such as molded medical grade polyurethane, and silicone. The sealing components of catheter 10 may be fabricated from low friction property materials such as, polytetrafluoroethylene (PTFE) coated, PTFE impregnated and/or internally lubricated elastomers. One skilled in the art, however, will realize that other materials and fabrication methods suitable for assembly and manufacture, in accordance with the present disclosure, also would be appropriate.

Catheter 10 may be installed in a subject through a subcutaneous tunneling procedure as disclosed in U.S. Pat. No. 4,832,687 to Smith, III and U.S. Pat. No. 5,944,732 to Raulerson, the entire contents of each of the '687 patent and the '732 patent being incorporated herein by reference. In one preferred embodiment, catheter 10 in implanted within a major vein of a patient via the reverse tunneling method disclosed in U.S. Pat. No. 5,509,897 to Twardowski, the entire contents of the '897 patent being incorporated herein by reference.

With initial reference to FIG. 11, extension tubes 16,18 with clamps 20 removed are placed in juxtaposed side by side relation as shown. As indicated hereinabove, the effective length of extension tube 16 and its adapter 56 is substantially equal to or less than the length of extension tube 18 such that the tubes 16,18 may be placed in side by side relation as shown in FIG. 11. Thereafter, extension tubes 16,18 may be optionally twisted onto each other to the configuration of FIG. 12. The twisting of extension tubes 16,18 serves to effectively secure the extension tubes 16,18 to each other thereby minimizing radial movement of the extensions tubes 16,18 during passage through the subcutaneous tunnel. In addition, with the extension tubes 16,18 secured, a tunneling or trocar instrument may be attached to a leading adapter 56 to facilitate passage of both extension tubes 16, 18 through the created tunnel.

Figure 15:
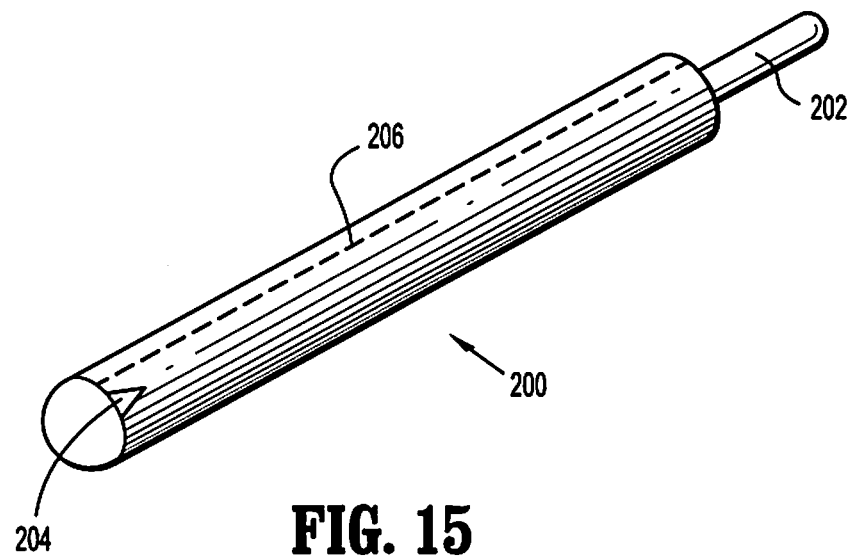
FIG. 15 is a perspective view illustrating an embodiment of the sheath of FIG. 14.

With reference to FIG. 13, a tunneling or trocar instrument 100 is operatively connected to the proximal or free ends of extension tubes 16,18 to effectively couple the tunneling instrument to catheter 10. In one preferred embodiment, tunneling instrument 100 includes mounting means in the form of, e.g., an internal threaded or cam lock 102, which cooperates with corresponding external thread 58 of adapter 56 to secure the tunneling instrument 100 to catheter 10. As a further alternative, a flexible sheath 200 may be positioned around the juncture or connection area of tunneling instrument 100 and adapter 56, preferably encompassing both adapters 56 as shown in FIG. 14. Sheath 200 facilitates passage of tunneling instrument 100 and catheter 10 through the subcutaneous tunnel by providing a smooth and flexible outer member which may readily traverse the created subcutaneous tunnel. Sheath 200 is preferably flexible and elastic to stretch and tightly fit over the components. FIG. 15 illustrates sheath 200 and with various features, for example, extension tab 202 which may be readily grasped to draw the sheath 200 back onto extension tube 16,18 once exposed from the tunnel. Slits or notches 204 in the sheath 200 are also envisioned. A tear away capability, for example along perforated or score line 206 may also be incorporated with sheath 200.

The use of system 10 will now be discussed in terms of a back end or reversed tunneling procedure in connection with hemodialysis treatment. In this regard low profile catheter 10 functions as a hemodialysis catheter. However, it is envisioned that the system may be used for other surgical treatments and in other deployment procedures. The preferred method will be discussed in terms of deployment of catheter 10 through the right jugular vein for positioning of within the right atrium. As appreciated, catheter 10 may be implanted in the right atrium via the left jugular vein, the right atrium through the right subclavian vein, the right atrium through the left subclavian vein, or implanted in the femoral vein of the subject.

Figure 18:
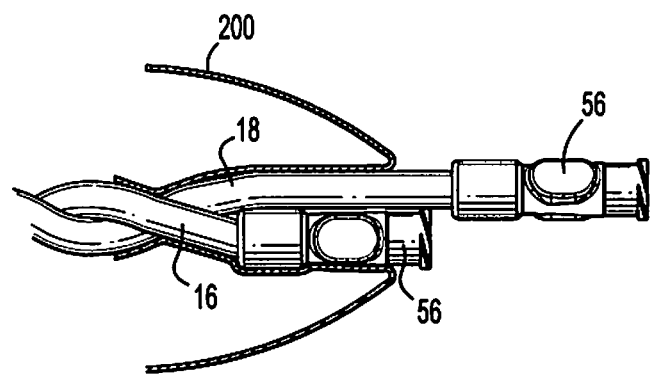
FIG. 18 is a view illustrating at least partial removal or retraction of the sheath to expose the adapters for connection to a hemodialysis machine.
Figure 17:
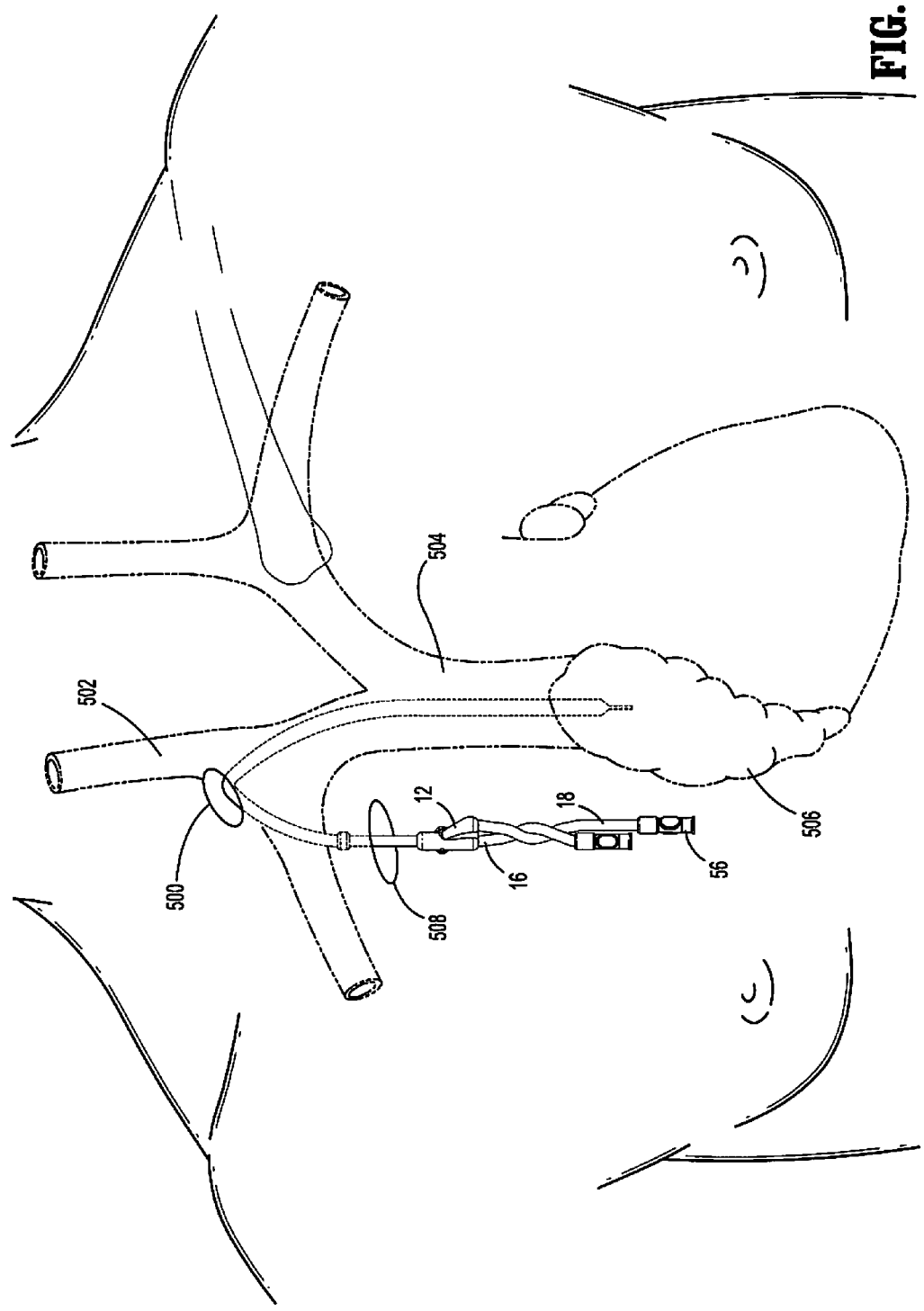

Referring now to FIG. 16, an incision or entry opening 500 is made adjacent the midclavicular line, through the skin and the subcutaneous tissue. The internal jugular vein 502 is punctured using known techniques and leading end 44 of catheter 10 in inserted through the internal jugular vein 502, the superior vena cavity 504 and into the right atrium 506. The positioning of leading end 44 may be confirmed with an x-ray if desired. Thereafter, a subcutaneous tunnel is made with, e.g., a tunneling device or trocar from the first incision area or entry opening area 500 downwardly to a lower chest area. A small exit opening 508 is made at the base of the subcutaneous tunnel. Thereafter, tunneling instrument 100 with attached catheter 10 and sheath 200 of FIG. 14 is maneuvered through the tunnel which correspondingly draws adapters 56, extension tubes 16,18, catheter hub 12 and the proximal end of elongated catheter member 14 through the tunnel toward the exit opening 508 as shown in FIG. 17. As appreciated, the narrow profile of catheter hub 12 facilitates passage of the catheter hub 12 through the subcutaneous tunnel. Tunneling instrument 100 is removed from adapter 56. With adapters 56, extension tubes 16, 18 and catheter hub 12 exposed from the exit opening 508, sheath 200 may be pulled back onto itself or removed to expose adapters 56 for connection to the appropriate fluid supply lines. FIG. 18 illustrates sheath 200 in the process of being pulled back on itself to expose adapters 56. As indicated hereinabove, extension tab 202 or notches 204 may be employed to facilitate this procedural step. Also, sheath 200 may be removed or separated from the components along, e.g., score line 206.

In a hemodialysis application, one adapter 56 may be connected to the hemodialysis machine to withdraw blood through, e.g., longitudinal lumen 38 and extension tube 16. The remaining adapter 56 is intended to return the blood through extension tube 18 and longitudinal lumen 40 for delivery to the right atrium area. Clamps 20 may be then mounted about extension tubes 16,18 and assembled in the manner discussed hereinabove. Clamps 20 may be manipulated between their respective first open and second closed positions as desired.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A catheter assembly comprising:
an elongated catheter defining first and second longitudinal lumens separated by a first septum wall extending from a proximal end to a distal end of the catheter along a longitudinal axis of the elongated catheter; and
a catheter hub comprising a proximal housing section and a distal housing section, the catheter hub defining a second septum wall, the proximal housing section defining first and second internal fluid conduits separated by the second septum wall, the first internal fluid conduit arranged about a first axis extending substantially parallel to a longitudinal hub axis, the second internal fluid conduit arranged about a second axis defining an oblique angle with respect to the longitudinal hub axis, and the distal housing section defining at least one lumen configured to receive the proximal end of the elongated catheter such that the first septum wall abuts the second septum wall and contacts an end of the second septum wall along the longitudinal axis of the elongated catheter, wherein the first internal fluid conduit is distally coextensive with the second internal fluid conduit, the first internal fluid conduit and the second internal fluid conduit each terminating at a proximal end of the at least one lumen of the distal housing section, and wherein the first septum wall is separate from the second septum wall.

2. The catheter assembly of claim 1, wherein the oblique angle with respect to the longitudinal hub axis is between about 5° and about 20°.

3. The catheter assembly of claim 1, wherein the longitudinal axis of the elongated catheter is a central longitudinal axis.

4. The catheter assembly of claim 1, wherein the first and second longitudinal lumens of the elongated catheter are coextensive with one another.

5. The catheter assembly of claim 1, wherein the elongated catheter defines a pair of opposed distal openings diametrically opposed to one another and in fluid communication with a respective one of the first and second lumens.

6. The catheter assembly of claim 5, wherein the first septum wall of the elongated catheter extends distally beyond the opposed distal openings.

7. The catheter assembly of claim 5, wherein the elongated catheter defines a pair of side openings proximal to the distal end openings and in fluid communication with a respective one of the first and second longitudinal lumens.

8. The catheter assembly of claim 1, wherein, when the first septum wall abuts the second septum wall, the first septum wall is substantially planar along the length of the elongated catheter.

9. The catheter assembly of claim 1, wherein each of the first and second lumens defines a D-shaped opening in cross-section.

10. The catheter assembly of claim 1, wherein an interference fit secures the proximal end of the elongated catheter within the distal housing section of the catheter hub.

11. The catheter assembly of claim 1, further comprising a pair of opposed suture wings along an outer surface of the catheter hub, the suture wings disposed proximal to the abutment between the first and second septum walls.

12. The catheter assembly of claim 1, wherein when the proximal end of the elongated catheter is received in the at least one lumen of the distal housing section, a proximal end of the first septum wall abuts a distal end of the second septum wall.

13. The catheter assembly of claim 1, wherein an end of the first septum wall contacts the end of the second septum wall.

14. The catheter assembly of claim 1, wherein the distal housing section defines a distal opening, the distal opening being open to the at least one lumen and to the first and second internal fluid conduits of the proximal housing section.

15. A catheter hub comprising:
a proximal housing section comprising a septum wall and defining first and second internal fluid conduits separated by the septum wall, the first internal fluid conduit arranged about a first axis extending substantially parallel to a longitudinal hub axis, the second internal fluid conduit arranged about a second axis defining an oblique angle with respect to the longitudinal hub axis, wherein the first internal fluid conduit is distally coextensive with the second internal fluid conduit; and
a distal housing section defining at least one lumen configured to receive a proximal end of an elongated catheter such that the septum wall abuts a septum wall of the elongated catheter and contacts an end of the septum wall of the elongated catheter along a longitudinal axis of the elongated catheter, the first internal fluid conduit and the second internal fluid conduit each terminating at a proximal end of the at least one lumen of the distal housing section, wherein the septum wall of the proximal housing section is separate from the septum wall of the elongated catheter, and wherein the septum wall of the elongated catheter extends along the longitudinal axis of the elongated catheter.

16. The catheter hub of claim 15, wherein the oblique angle with respect to the longitudinal hub axis is between about 5° and about 20°.

17. The catheter hub of claim 15, wherein the longitudinal axis of the elongated catheter is a central longitudinal axis.

18. The catheter assembly of claim 15, wherein an end of the septum wall of the proximal housing section contacts the end of the septum wall of the elongated catheter.

19. The catheter assembly of claim 15, wherein the distal housing section defines a distal opening, the distal opening being open to the at least one lumen and to the first and second internal fluid conduits of the proximal housing section.

20. A catheter assembly comprising:
an elongated catheter defining first and second longitudinal lumens separated by a first septum wall extending from a proximal end to a distal end of the catheter along a longitudinal axis of the elongated catheter; and
a catheter hub comprising a proximal housing section and a distal housing section, the catheter hub defining a second septum wall, the proximal housing section defining first and second internal fluid conduits separated by the second septum wall, the first internal fluid conduit arranged about a first axis extending substantially parallel to a longitudinal hub axis, an oblique angle defined between the first internal fluid conduit and the second internal fluid conduit, and the distal housing section defining at least one lumen configured to receive the proximal end of the elongated catheter such that the first septum wall abuts the second septum wall and contacts an end of the second septum wall along the longitudinal axis of the elongated catheter, the first internal fluid conduit and the second internal fluid conduit each terminating at a proximal end of the at least one lumen of the distal housing section, and wherein the first septum wall is separate from the second septum wall.

21. The catheter assembly of claim 20, wherein the first internal fluid conduit and the second internal fluid conduit each terminate at a distal end of the second septum wall.

22. The catheter assembly of claim 20, wherein the first internal fluid conduit and the second internal fluid conduit each terminate at a proximal end of the second septum wall.

23. The catheter assembly of claim 20, wherein the first internal fluid conduit and the second internal fluid conduit are longitudinally coextensive with one another.

24. The catheter assembly of claim 20, wherein an end of the first septum wall contacts the end of the second septum wall.

25. The catheter assembly of claim 20, wherein the distal housing section defines a distal opening, the distal opening being open to the at least one lumen and to the first and second internal fluid conduits of the proximal housing section.

* * * * *